United States Patent [19]
Nordlund et al.

[11] Patent Number: 5,719,126
[45] Date of Patent: Feb. 17, 1998

[54] MELANOGENIC INHIBITOR, AND METHODS OF PRODUCING AND USING THE SAME

[75] Inventors: James J. Nordlund, Cincinnati; Jamal Z. Farooqui, West Chester, both of Ohio

[73] Assignee: University of Cincinnati, Cincinnati, Ohio

[21] Appl. No.: 446,600

[22] PCT Filed: Nov. 16, 1993

[86] PCT No.: PCT/US93/11139

§ 371 Date: May 24, 1995

§ 102(e) Date: May 24, 1995

[87] PCT Pub. No.: WO94/12534

PCT Pub. Date: Jun. 9, 1994

[51] Int. Cl.[6] ........................................ A61K 38/00
[52] U.S. Cl. ........................... 514/12; 530/350; 530/412; 530/416
[58] Field of Search .................. 514/12; 530/350, 530/412, 416

[56] References Cited

U.S. PATENT DOCUMENTS 5,331,091  7/1994  Fukuda et al. ..................... 530/350

FOREIGN PATENT DOCUMENTS 0389950  10/1990  European Pat. Off. .
2213061  8/1989  United Kingdom .

OTHER PUBLICATIONS

Farooqui et al., "The Isolation of a Unique Melanogenic Inhibitor . . . ", Pigment Cell Research, vol. 6, No. 4, pp. 299–300, Aug. (1993), abstract.
Madsen et al., The Journal of Investigative Dermatology, vol. 99, No. 3, pp. 299–305, Sep. 1992.
Rasmussen et al., Elcetrophoresis 13: 960–969 (1992).
"Regulation of Melanin Pigmentation by Tyrosinase, TRP1, TRP2, and a Melanogenic Inhibitor," Koichiro Kameyama, Jun. 18–20, 1992.
"Skin Bleaching Preparations," S.S. Bleehen, 28 J. Soc. Cosmet. Chem. 407–412 (1977) © 1977 Society of Cosmetic Chemists of Great Britian.
"Evaluation of Skin Bleach Creams," K.V. Curry, 25 J. Soc. Cosmet. Chem 339–354 (1974) Society of Cosmetic Chemists of Great Britian.

Abstract: "Hyperpigmentation of Human Xenografts on Albino Nude Mice," Billye W. Auclair, PanAmerican Society for Pigment Cell Research, Apr. 23–26, 1989.

"Molecular Cloning And Expression Of A Novel Keratinocyte Protein (Psoriasis–Associated Fatty Acid–Binding Protein (PA–FABP) That Is Highly Up–Regulated In Psoriatic Skin And That Shares Similarity To Fatty Acid–Binding Proteins," Madsen, et al., The Journal of Investigative Dermatology, vol. 99, No. 3, pp. 299–305, Sep. (1992).

Abstract of Article: "Immune And Nonimmune Effector Functions Of IgG3 Mouse Monoclonal Antibody R24 Detecting The Disialoganglioside GD3 On The Surface Of Melanoma Cells," Welt, et al., File Server STN Karlsruhe, File Medline Abstract No. 88028034, Clin. Immunol. Immunopathol., Nov. (1987).

Abstract of Japanese Patent: "Preparation Inhibits Melanogenesis And Activates Fibroblasts Proliferation–containing protein or glyco: protein hydrolysate of cuttlefish ink as active cmponent"; JP–A 3 255 016 (Sancho Pharm KK), Nov. 13, 1991, Database WPI, Section CH, Week 9201. Derwent Publications Ltd., Lond, GB; Class B04, AN 92–002611.

Abstract of Article: "Human Skin Xenografts Express A Potent Epidermal Melanogenic Inhibitor," Farrooqui et al., Clinical Research, vol. 41, No. 3, Oct. (1993).

Abstract of Article: "The Isolation Of A Unique Melanogenic Inhibitor From Human Skin Xenografts," Farrooqui et al., Pigment Cell Research, vol. 6, No. 4, pp. 299–300, Aug. (1993).

Primary Examiner—Cecilia J. Tsang
Assistant Examiner—C. Delacroix-Muirheid
Attorney, Agent, or Firm—Frost & Jacobs

[57] ABSTRACT

A purified, naturally derived melanogenic inhibitor protein capable of inhibiting melanogenesis in pigmentary cells has an amino acid sequence SEQ ID NO: 4. A method of producing melanogenic inhibitor protein comprises grafting mammalian skin onto a live host, permitting the mammalian skin to remain on the host for a predetermined period of time, removing the mammalian skin, and extracting the protein from the skin. Methods of controlling melanogenesis in pigmentary cells or selectively destroying melanoma cells comprise the steps of mixing an effective amount of melanogenic inhibitor protein, or an active segment, derivative, or analog thereof, with a suitable carrier, and applying this mixture to the pigmentary or melanoma cells.

19 Claims, No Drawings

MELANOGENIC INHIBITOR, AND METHODS OF PRODUCING AND USING THE SAME

TECHNICAL FIELD

This invention relates to a melanogenic inhibitor, and methods of producing and using the same. More specifically, this melanogenic inhibitor comprises a naturally derived protein, or effective segments thereof, which reduces tyrosinase activity, inhibits pigmentary cell proliferation, and is cytotoxic to melanoma cells.

BACKGROUND ART

Hyperpigmentary disorders affect many people worldwide, and are often the cause of much embarrassment or worse. These disorders include such things as: freckles, solar lentigines (livers spots), the visible darkening that often occurs in skin grafted onto burn victims, and, most serious of all, melanoma. Additionally, many also desire to lighten their basal skin tone merely for cosmetic reasons.

Various means have been utilized in the past for either reducing pigmentation in hyperpigmented areas or for lightening basal skin tone. While mixed results have been obtained with these treatments, most can result in undesirable side-effects. Compounds that have been used for bleaching, or depigmenting, skin include: hydroquinone, derivatives of hydroquinone, ammoniated mercury, ascorbic acid, mercaptoamines, 4-isopropylcatechol, and peroxides. None, however, have proven to be completely reliable and without side effects.

European Patent Application 389,950 discloses a melanocyte-stimulating hormone (MSH) inhibitor that is reported to be useful for such things as preventing or relieving the symptoms of chloasmata or freckles. This inhibitor contains an amino acid sequence represented by the following formulas: -His-Ser-Arg-Trp-; Trp-Arg-Ser-His-; or -Leu-Ala-Cys-Ala-Arg-. The peptides represented by the first two of these sequences have an affinity for the MSH receptor contained on the surface of melanocytes, and thereby antagonize MSH. Peptides represented by the third sequence have an affinity for MSH itself, and thereby inhibit the effect of MSH.

Subsequent to their invention, Applicants have become aware of a recent publication which discloses a protein that may be related to that which they have produced (Madsen, P. et al., I. Invest Dermatol 99:299–305 (1992)), and in fact may be identical. This protein is reported to be highly up-regulated in psoriatic keratinocytes, however no relationship to melanogenesis is mentioned.

A more serious skin hyperpigmentary disorder that effects millions worldwide is melanoma. While it can sometimes be treated if detected early, melanoma is often fatal. Currently available treatments, such as chemotherapy, often cause serious side effects, and are never completely effective in all instances.

Heretofore, however, there has not been an available naturally derived composition that can reliably inhibit melanogenesis and thereby reduce skin pigmentation, is selectively cytotoxic to melanoma cells, and has no known side effects.

SUMMARY OF THE INVENTION

While not exclusive, the following describes some of the important features and objects of the present invention.

It is an object of the present invention to provide a naturally derived melanogenic inhibitor useful for reducing pigmentation in skin and selectively destroying melanoma cells.

It is also an object of the present invention to provide a naturally derived melanogenic inhibitor comprising a naturally derived melanogenic inhibitor protein, or active segments thereof.

It is a further object of the present invention to provide a method for producing a melanogenic inhibitor protein.

It is yet another object of the present invention to provide a method for controlling pigmentation in skin and/or hair utilizing a naturally derived melanogenic inhibitor protein, or active segments thereof.

It is another object of the present invention to provide a method for destroying melanoma cells, without affecting normal, nonpigmentary cells, utilizing a naturally derived melanogenic inhibitor protein, or active segments thereof.

As used herein, "melanogenesis" means the formation of melanin by living cells, and "inhibiting melanogenesis" includes inhibiting the ability of individual cells to produce melanin and/or decreasing the population of cells capable of producing melanin.

In accordance with one aspect of the invention, there is provided a heretofore unknown naturally derived protein capable of inhibiting melanogenesis in pigmentary cells and selectively destroying melanoma cells without harming other cells. This melanogenic inhibitor (MI) protein has the following amino acid sequence which is shown in conjunction with the corresponding codon (the numbers below each amino acid refer to the location of the amino acid in the MI sequence):

```
SEQ ID NO: 3:
ATG GCC ACA GTT CAG CAG CTG GAA GGA AGA TGG CGC CTG GTG
Met Ala Thr Val Gln Gln Leu Glu Gly Arg Trp Arg Leu Val
1             5                      10

GAC AGC AAA GGC TTT GAT GAA TAC ATG AAG GAG CTA GGA GTG
Asp Ser Lys Gly Phe Asp Glu Tyr Met Lys Glu Leu Gly Val
15            20                     25

GGA ATA GCT TTG CGA AAA ATG GGC GCA ATG GCC AAG CCA GAT
Gly Ile Ala Leu Arg Lys Met Gly Ala Met Ala Lys Pro Asp
     30                 35                 40

TGT ATC ATC ACT TGT GAT GGT AAA AAC CTC ACC ATA AAA ACT
Cys Ile Ile Thr Cys Asp Gly Lys Asn Leu Thr Ile Lys Thr
        45                 50                 55

GAG AGC ACT TTG AAA ACA ACA CAG TTT TCT TGT ACC CTG GGA
Glu Ser Thr Leu Lys Thr Thr Gln Phe Ser Cys Thr Leu GLY
           60                 65                 70
```

-continued

```
GAG AAG TTT GAA GAA ACC ACA GCT GAT GGC AGA AAA ACT CAG
Glu Lys Phe Glu Glu Thr Thr Ala Asp Gly Arg Lys Thr Gln
                75                  80

ACT GTC TGC AAC TTT ACA GAT GGT GCA TTG GTT CAG CAT CAG
Thr Val Cys Asn Phe Thr Asp Gly Ala Leu Val Gln His Gln
85                  90                  95

GAG TGG GAT GGG AAG GAA AGC ACA ATA ACA AGA AAA TTG AAA
Glu Trp Asp Gly Lys Glu Ser Thr Ile Thr Arg Lys Leu Lys
    100                 105                 110

GAT GGG AAA TTA GTG GTG GAG TGT GTC ATG AAC AAT GTC ACC
Asp Gly Lys Leu Val Val Glu Cys Val Met Asn Asn Val Thr
        115                 120                 125

TGT ACT CGG ATC TAT GAA AAA GTA GAA TAA
Cys Thr Arg Ile Tyr Glu Lys Val Glu
            130                 135
```

For the sake of clarity, the sequence for the entire MI protein is shown below:

SEQ ID NO.: 4:
```
Met Ala Thr Val Gln Gln Leu Glu Gly Arg Trp Arg Leu Val
1               5                   10

Asp Ser Lys Gly Phe Asp Glu Tyr Met Lys Glu Leu Gly Val
15              20                  25

Gly Ile Ala Leu Arg Lys Met Gly Ala Met Ala Lys Pro Asp
    30                  35                  40

Cys Ile Ile Thr Cys Asp Gly Lys Asn Leu Thr Ile Lys Thr
            45                  50                  55

Glu Ser Thr reject grafts of distinct phylogenetical origin, and they have been used extensively in the study of human skin. Human skin grafted onto nude mice maintains its structural and immunological identity, and also some of its major functional properties.

In this discussion and all of the examples that follow, viable donor skin was obtained from caucasian adult cadavers. The skin was removed using a dermatome at a thickness of 12–14/1000th of an inch, and stored in F-12 tissue culture media (available from Gibco Laboratories, of Grand Island, N.Y.) at 4° C. The nude mice were first anesthetized using Nembutol, and graft sites were prepared by removing the skin from the appropriate area of the torso. Split-thickness (12–14/1000th of an inch) donor skin was then positioned in the appropriate location on the mice and sutured in place. Grafts were attached to the mice within 48 hours after the death of the donor. When necessary, xenografts were removed from the mice using sterile surgical techniques, after the mice were sacrificed with an overdose of Nembutol.

As expected, the xenografts exhibited the same hyperpigmentation that has been reported in burn patients. Various histological tests and examinations were performed on the xenografts prior to the grafting itself, as well as at various times post-grating, in order to study this observed hyperpigmentation. Visible darkening of the xenografts occurred as early as two weeks post-grafting, and, although there were observable differences, all of the xenografts exhibited hyperpigmentation. The observed hyperpigmentation, however, was restricted to the xenograft, and did not extend into the host skin.

Microscopic analysis of xenograft samples revealed a significant increase in the number of DOPA positive melanocytes in the xenografts as compared to that noted prior to grafting. A DOPA positive melanocyte is one in which functional tyrosinase is present, and is thus producing pigment. While there was some variability in the extent of the increase, there was at least a three-fold increase in the number of DOPA positive melanocytes, and all of the samples exhibited a peak at around six weeks post-grafting. From that point on, the number of DOPA positive melanocytes steadily declined, however it remained slightly elevated in some xenografts as late as 30 weeks post-grating.

The size of the melanocytes cell bodies in the xenografts was also measured as an indicator of melanogenic activity. In all cases, the size of the melanocytes more than doubled over that seen in the pre-grafting samples, and once again exhibited a peak followed by a gradual decline. In addition, the dendricity of the melanocytes also markedly increased in the xenografts. An increase in dendricity will generally result in an increase in skin pigmentation, as the dendrites are responsible for transferring melanin to the epidermis. While the degree of hyperpigmentation did not always correlate with the number of DOPA positive melanocytes, it did tend to correlate with the dendricity of the melanocytes. This would tend to indicate that the observed hyperpigmentation is more a result of increased melanogenic activity than an increase in the actual number of melanocytes.

SDS-PAGE analysis of both pre- and post-grafting human skin extract was performed in order to determine if there were any differences in both low and high molecular weight protein profiles. While there were no obvious differences in protein patterns between samples taken at various times post-grafting, a protein band with an apparent molecular weight of approximately 13 to 14 kDa was exclusively expressed in the post-grafting xenograft samples and was not found in the pre-grafted skin. Interestingly, a protein of similar molecular weight was also found in nude mouse skin extract. The 13 to 14 kDa protein band appeared as early as 2 weeks post-grafting, and continued to be expressed more than 14 weeks post-grafting.

In the examples that follow, various protein fractions and purified proteins were applied to several different types of cells in order to determine the effect on pigmentary function, if any, of proteins extracted from both pre- and post-grafting skin. Pre-grafting skin simply refers to normal human skin, while post-grafting skin refers to live xenografts supported by nude mice. The culmination of this testing has been the isolation of a unique Melanogenic Inhibitor (MI) protein obtained from the 13 to 14 kDa band referred to above. While the applicants are not certain as to MI protein affects melanogenesis and selectively destroys melanoma cells, there is reason to believe that these effects are mediated through MSH and/or its receptor.

EXAMPLE 1

The first cell type employed was Cloudman S91 melanoma, a moderately melanotic murine cell that has been used extensively to study melanogenesis and pigmentary cell growth. The melanoma cells were maintained in monolayer cultures in Ham's F-10 medium (available from Gibco Laboratories, of Grand Island, N.Y.) supplemented with 10% heat-activated mouse serum, 2.5% heat activated fetal calf serum, 100 units/ml penicillin, and 100 µg/ml streptomycin, at 37° C. in a humified incubator containing 5% $CO_2$. Cells were subcultured weekly, and maintained in the culture for only 10 passages in order to avoid phenotypic drift. Monolayer stock cultures were regenerated from cells that were cryopreserved in liquid nitrogen (as described by Zalfa Abdel-Malek et al., Cancer Research 47:3141–6 (1987)).

Protein extracts from both pre- and post-grafting (12 to 15 weeks after grafting) skin samples were prepared by first removing the underlying fat and then cutting the skin sample into small pieces. A 20–30% homogenate in phosphate buffer saline (PBS) containing 1 mM PMSF was prepared by homogenizing the skin using a polytron. After centrifugation at 2000 x g for 20 minutes, the crude extract was removed and further centrifuged at 100,000 x g for one hour to obtain a clear soluble supernatant fraction. The supernatant was filter sterilized, and the protein content determined by Bio-Rad's method.

The Cloudman S91 melanoma cells were then harvested by replacing the culture medium with Tyrodes solution containing EDTA. Cells were seeded at a density of about $0.2 \times 10^6$ cells/25 $cm^2$ in each flask. Triplicate flasks were used for each experimental group, and control flasks were also utilized. After 24 hours, this medium was replaced with fresh medium containing various concentrations of pre- or post-grafted supernatant prepared as above, and the solutions were incubated for 24 hours. Finally, fresh medium containing $^3$H-tyrosine (1 µCi/ml) and supernatant (in the same concentration as previously used) was added, and the solutions incubated for another 24 hours. The tyrosine hydroxylase activity of tyrosinase was then measured in situ according to a modified Pomerantz charcoal absorption method (as described by Fuller, B. B. & Viskochil, B. H., Life Sci. 24:2405–2416 (1979)). This assay measures tyrosinase activity by measuring the amount of $^3H_2O$ released after $^3$H-tyrosine is converted to L-DOPA by tyrosinase, and is a significant indicator of melanogenic activity since a reduction in tyrosinase activity will result in a corresponding reduction in melanogenesis (i.e. reduced skin pigmentation).

Melanoma cells treated with 25 µg/ml of post-grafting protein extract exhibited an increase in tyrosinase activity of approximately 20%, as compared to the control. Concentrations less than 25 µg/ml did not increase the tyrosinase activity any further. At higher concentrations of post-grafting protein extract, however, the tyrosinase activity in the melanoma cells was reduced in a dose-dependent fashion. The reduction in tyrosinase activity was approximately 20% at a 50 µg/ml concentration, 30% at 75 µg/ml, and 50% at 100 µg/ml. In contrast, the melanoma cell cultures treated with pre-grafted skin protein extract did not exhibit any statistically significant change in tyrosinase activity. Thus, it is apparent that the production of a potent inhibitor of melanogenesis is induced when human skin is grafted onto a live host, and this inhibitor is present in the protein extract from the post-grafting skin.

EXAMPLE 2

The effect of the protein extracts of Example 1 on normal human melanocytes was also examined. Normal melanocytes were obtained by first removing the subcutaneous tissue from the ventral surface of neonatal foreskin. The tissue was then incubated in 0.25% trypsin at 4° C. overnight. Next, the epidermis was manually split from the dermis, and both were vigorously vortexed in growth medium. The supernatant was then removed and transferred onto a 25 cm$^2$ tissue flask (procedure further described by Zalfa Abdel-Malek et al., Journal of Cellular Physiology, 150:416–25 (1992)). The growth medium employed in both the extraction referred to above and in the maintenance of the cells comprised: Ham's F-10 medium, $10^{-4}$M IBMX, 5% heat-inactivated fetal calf serum, 5% newborn calf serum, 5 µg/ml insulin, 2 µg/ml α-tocopherol, 2 µg/ml transferrin, 5 ng/ml TPA, 20 ng/ml cholera toxin, 10,000 units/ml penicillin, and 10,000 µg/ml streptomycin. Once again the cells were maintained at 37° C. in a humified incubator containing 5% $CO_2$. Melanocytes were then seeded into 6 cluster wells (9.6 cm$^2$ surface area) at a density of $0.15 \times 10^6$ cells/well. The remaining steps of Example 1, including the extraction of pre- and post-grafting (12 to 15 weeks) skin protein extracts, were the same.

Tyrosinase activity in the normal melanocyte cells was measured for various concentrations of protein extract treatments (25–100 µg/ml). Once again the same low-concentration increase in tyrosinase activity and subsequent dose-dependent decrease in tyrosinase activity at higher concentrations of post-grafting protein extract was observed. The change in tyrosinase activity observed for each concentration was approximately the same as that recorded for the melanoma cells in Example 1, with a 50% reduction in tyrosinase activity observed for cells incubated in 100 µg/ml post-grafting protein extract. The cells treated with pre-grafted skin protein extract did not show any statistically significant change in tyrosinase activity. Thus, the melanogenic inhibitor present in the post-grafting skin protein extract has identical inhibiting effects in both normal melanocytes and melanoma cells.

EXAMPLE 3

In order to examine the various proteins contained in the pre- and post-grafted skin protein extracts, one-dimensional 0.1% SDS-PAGE analysis was performed. The discontinuous buffer system described by Laemmli (reported in Nature 227: 680–5 (1970)) was employed using a 15% acrylamide gel. Cells were stained with Coomassie brilliant blue R-250 in order to visualize the protein bands. Both crude extract (2000 x g) and supernatant (100,000 x g) from pre- and post-grafting skin (prepared in the manner described in Example 1) were subjected to analysis. Additionally, the pellet remaining after the 100,000 x g centrifugation was extracted with triton X-100 to solubilize any particulate fraction, and likewise subjected to SDS-PAGE.

No obvious differences were observed between the protein profiles or pre-grafted crude extract and supernatant. Likewise, there were also no obvious differences between post-grafting crude extract and supernatant. There were, however, significant differences between the protein profiles of pre- and post-grafting samples. Most significantly was the appearance of a 13 to 14 kDa doublet exclusively present in the post-grafting skin samples. Furthermore, the fraction extracted from the pellet with triton X-100 did not contain this protein band, an indication that this band contains soluble protein(s). The dermis and epidermis of post-grafting skin were also split from one another, and the steps above repeated. The 13–14 kDa protein band was present in both samples, however it was expressed to a greater extent in the epidermis.

The above analysis was also performed utilizing post-grafting skin that had remained on its host for varying lengths of time. The 13–14 kDa protein band appeared as early as 2 weeks post-grafting, and continued to be expressed more than 14 weeks post-grafting.. No significant differences were noted in protein patterns even between sample from 2 and 14 weeks post-grafting.

EXAMPLE 4

In order to determine if the 13–14 protein band comprises multiple proteins, two-dimensional polyacrylamide gel electrophoresis was performed on both pre- and post-grafting skin supernatant. The supernatant extract from post-grafting skin (obtained in the manner described in Example 1) was first, however, subjected to ion-exchange chromatography using a DEAE-cellulose column (15cm×1.5 cm). The supernatant (15 ml) was loaded onto the column, and the column was washed with phosphate buffer to elute the unbound proteins. Fractions containing 5ml of solution were taken every 5 minutes, and the absorbance at 280 nm was measured for each collected fraction. The column was washed with phosphate buffer until the absorbance of the eluting fractions was near negligible. Thereafter, the bound proteins were eluted from the column by a salt gradient (NaCl in phosphate buffer) of 0 to 1.0M. Spectroscopic analysis of the fractions indicated the presence of two distinct absorbance peaks (at 280 nm).

Next, the fractions associated with each of the two peaks were pooled and dialyzed extensively against double distilled water containing 0.02% sodium azide for at least 36 hours. The dialyzed peaks were then lyophilized overnight to obtain dried powder. The powders were then dissolved in distilled water and protein contents determined. These two peak fractions were then each subjected to two-dimensional SDS-PAGE analysis.

In order to perform two-dimensional SDS-PAGE analysis, aliquots of the two peak fractions containing 700–800 µg of protein were lyophilized. The two samples were then solubilized in 9M urea containing 2% CHAPS detergent (available from Sigma Chemical Co.). and 2% each of ampholine (pH 3–10) and β-merceptoethanol, and incubated for 2 hours at room temperature. After centrifugation at 14,000 rpm for 15 minutes, the samples were loaded onto isoelectric focusing gels. Isoelectric focusing was carried out using ampholine pH 3–0 overnight at 700 volts (as described by Farrell, J. Biol. Chem. 250: 4007–21, (1975)). The gels were then equilibrated in SDS-equilibrating buffer for at least 15 minutes before loading into the slab gel for second-dimensional SDS-PAGE using 15% gel. The gels were stained with Coomassie blue to visualize the various protein spots.

In the supernatant samples obtained from post-grafting skin, the 13–14 kDa protein band of the first absorbance peak fraction was resolved into four distinct protein spots having pI (isoelectric point) values in the range of 6.5 to 7.5. The second absorbance peak solution, however, did not exhibit any proteins in this molecular weight range. Likewise, when the preceding steps were repeated for pre-grafted skin, these proteins were not expressed. Thus, it is apparent that the 13–14 kDa protein band found in post-grafting skin actually comprises four distinct proteins.

EXAMPLE 5

In order to isolate and test the four proteins contained in the 13–14 kDa protein band, electroelution was employed. Unstained gels obtained by the one-dimensional SDS-PAGE procedures of Example 3 using post-grafting skin supernatant were aligned side by side with stained gels (as a marker), and the 13–14 kDa protein band was cut from the unstained gels. The gels were then cut into small pieces and transferred into the electroelution chamber of a Schleicher and Schuell electroelution apparatus (available from S.S. Inc., Keene, N.H.) A buffer system comprising 20 mM Tris, 150 mM glycine, and 0.05% SDS was added, and electroelution was carried out overnight at 150 volts. The electroeluted fractions were then collected, concentrated and dialyzed using a Centricon-3 concentrator (available from Amicon Corp., division of W.R. Grace & Co., Beverly, Mass.) to a volume of about 0.5 ml. Finally, this concentrated 13–14 kDa protein mixture was filter sterilized and its protein contents determined.

The procedures of Example 1 were followed in order to examine the effect on tyrosinase activity in melanoma cells of the electroeluted proteins. The 13–14 kDa protein mixture obtained from post-grafting skin supernatant was added to the cell cultures in concentrations ranging from 0.25 to 1.0 µg/ml. In order to ensure that any observed effects were indeed due to the protein mixture present in the 13–14 kDa band from post-grafting skin, the entire procedure was also performed for supernatant from pre-grafted skin.

The 13–14 kDa protein mixture obtained from post-grafting skin caused rather significant dose-dependent reductions in tyrosinase activity in the melanoma cells. In fact, this reduction was almost 90% at a protein concentration of 1.0 µg/ml. In contrast, the tests using corresponding amounts of solutions obtained from pre-grafted skin supernatant resulted in only slight, insignificant reductions in tyrosinase activity.

When these same tests were repeated using normal human melanocytes (obtained by the methods of Example 2), the 13–14 kDa protein mixture likewise caused a reduction in tyrosinase activity. At a concentration of 0.25 µg/ml, a reduction in tyrosinase activity of approximately 37% was observed; at 0.5 µg/ml, the observed reduction was approximately 53%. Very little reduction of tyrosinase activity was observed when extract from pre-grafted skin was employed. These results indicate that the melanogenic inhibitor present in post-grafting skin extract is contained in the 13–14 kDa electroeluted protein mixture.

EXAMPLE 6

The effect of pre- and post-grafting skin extracts on cell proliferation was assessed by measuring the rate of $^3$H-thymidine incorporation, which is a measurement of the rate of DNA synthesis within the cell. Obviously, a reduction in melanocyte proliferation will cause a corresponding reduction in observed skin pigmentation, since the melanocytes are directly responsible for pigment production. Cloudman melanoma cells were seeded into a 96-well flat-bottom culture plate in a volume of 200 µl/well. Cells in F-10 growth medium were permitted to attach, and on the following day half of the volume of medium was replaced with 100 µl fresh medium and a selected amount of skin protein extract. Each experimental group consisted of 6 wells. After 24 hours of treatment, half the medium was again replaced with fresh medium and skin protein extract. During this latter treatment period, the cells were pulsed labeled with $^3$H-thymidine (1 µCi/well).

After 24 hours incubation, the cells were harvested onto glass fiber filters using a semi-automated PHD cell harvester (available from Cambridge Technology). The filters were air dried overnight, transferred individually to scintillation vials, and treated with 450 µl Protosol tissue and gel solubilizer. The vials were then warmed in an oven at 66° C. for 75 minutes, then allowed to cool. Next, 100 µl of glacial acetic acid and 9.5 ml EconoFluor-2 (a non-aqueous scintillant) were added to each vile. The viles were allowed to cool in a refrigerated scintillation counter for 24 hours, and counts were then taken for one minute.

In the samples employing the 13–14 kDa protein mixture (electroeluted as in Example 5), a dose-dependent inhibition of melanoma cell proliferation (as compared to control samples) was observed. This inhibition was more than 30% at a protein mixture concentration of 0.25 µg/ml, and was nearly 50% at a concentration of 0.50 µg/ml. In contrast, melanoma cells treated with extract from pre-grafted skin exhibited a slight, insignificant reduction in cell proliferation. Normal human melanocyte cell proliferation was also inhibited by the 13–14 kDa protein mixture to the same extent when these tests were repeated with normal melanocytes. Likewise, the pre-grafted skin extract did not inhibit cell proliferation in normal melanocytes.

Melanoma cells were also observed after the incubation period under a phase contrast microscope in order to study their morphology. In the untreated cells (control) and those treated with extract from pre-grafted skin, the cells appeared to be normal and healthy, with prominent dendrites extending between cells and forming the characteristic network. In contrast, the cells treated with the 13–14 kDa protein mixture were not healthy, and numerous non-attached, floating dead cells were present. In fact, only about 40% of the cells remained viable, and cell density was greatly reduced. Additionally, very few dendrites extended from the remaining cells, and virtually all were round in shape. This is a clear indication that, not only does the melanogenic inhibitor inhibit pigmentary cell proliferation, it is also cytotoxic to melanoma cells.

EXAMPLE 7

In order to determine if the 13–14 kDa protein mixture isolated from post-grafting skin was merely a general metabolic inhibitor, $^3$H-thymidine cell proliferation testing was repeated using normal human fibroblasts. Normal human diploid neonatal foreskin fibroblasts were purchased from Clonetics Corporation, and, upon arrival, they were fed Dulbeeco's Modified Eagle Medium (DMEM) supplemented with 10% fetal bovine serum in T-25 flasks. After three days of incubation at 37° C., the fibroblasts were trypsinized and seeded into 48-well microtiter plates at 3,000 cells per square centimeter. The plates were then incubated at 37° C. for three days. Next, the media was changed to 0.2% serum in DMEM and the cells remained in this environment for 4 to 5 days with no other additions.

Two types of assays were performed: agonist and antagonist. In the agonist assay, various concentrations of the post-grafting skin protein extract were added to randomly selected wells. Fibroblast Growth Factor (FGF) was used as a positive control. Tritiated thymidine (to study proliferation) or tritiated proline (to study collagen production) was also added. The cells were incubated in this media for 2 days (proliferation) and 4 days (collagen production), respectively. The media was then removed and the cells washed and then lysed with SDS. One ml of this lysate was added to 9 ml of scintillation cocktail and counted. For the antagonist assays the same procedure was followed except that FGF was also added to each well that contained the protein mixture to determine if the active component of the mixture competed with FGF and displayed a resultant decrease in tritiated thymidine or tritiated proline incorporation. The protein extract exhibited no effect on proliferation and collagen production in either the agonist or antagonist assays, regardless of concentration. Therefore, it is apparent that the effects of the 13–14 kDa protein mixture are specific for pigmentary cells, and the melanogenic inhibitor present in this mixture is not merely a general metabolic inhibitor.

EXAMPLE 8

Since the studies described in Example 4 indicated that the melanogenesis inhibiting 13–14 kDa protein mixture actually comprises four distinct proteins, tests were undertaken to determine which of these proteins was responsible for the observed effects. Post-grating skin supernatant was fractionated using a DEAE-cellulose ion exchange column as in Example 4. The fractions corresponding to the first peak (as discussed in Example 4) were collected and pooled, and the mixture was then dialyzed and lyophilized. Two-dimensional SDS-PAGE, as described in Example 4, was then performed in order to separate the protein mixture into the four distinct proteins previously found. The gels were then stained with Coomasie blue, and the four protein "spots" obtained were individually cut from the gels. Each of the four proteins were then electroeluted from the gels (as described previously) and concentrated. Protein contents of the resulting solutions were also determined. In this manner, the four purified (isolated from each other) proteins were obtained.

Both tyrosinase activity and $^3$H-thymidine incorporation in Cloudman melanoma cells were studied using the procedures outlined previously. A protein concentration of approximately 1.0 μg/ml of each of the four purified proteins was utilized in these tests, and, as controls, both untreated cell cultures and α-MSH ($10^{-7}$ M) treated cultures were included in the experiment. Tyrosinase activity was reduced by approximately 40% in the cultures treated with purified protein corresponding to the third protein "spot". Cultures treated with the other three proteins, on the other hand, did not exhibit any significant decrease in tyrosinase activity. Similarly, cell proliferation was significantly inhibited (approximately 45%) in the presence of the purified protein corresponding to the third "spot", while the other proteins had no significant effect on cell proliferation.

Based upon these tests, it is apparent that the protein electroeluted from the third gel "spot" is responsible for the melanogenesis inhibition and cell proliferation inhibition previously observed. The previous two-dimensional SDS-PAGE analysis indicated that this Melanogenic Inhibitor ("MI") protein corresponding to the third "spot" has a molecular weight of approximately 14,000, and an isoelectric point of between about 7.2 and about 7.5.

EXAMPLE 9

To determine the amino acid sequence of the four proteins contained in the 13–14 kDa protein mixture, two-dimensional SDS-PAGE analysis was once again performed on the fractionated post-grafting skin extract in the manner described previously. Proteins were blotted onto Immobilon PSQ (a PVDF membrane) and visualized after staining with Amido black. Each of the four "spots" was then excised from the blot and reacted with iodoacetamide before sequencing. Protein sequencing was performed on an Applied Biosystems 475A protein sequencer using pulsed-liquid chemistry (Speicher, D. W., (1989), *Techniques in Protein Chemistry*, (T. E. Hugh, Ed.), Academic Press, San Diego, Calif., pp. 24–35).

Partial N-terminal amino acid sequence analysis of the first "spot" indicated that this protein is identical to mouse transthyretin, or prealbumin. Transthyretin is a serum protein having a molecular weight of 55 kDa, however it is composed of four identical subunits having a molecular weight of approximately 14 kDa. The sequence analysis of the second "spot" indicates that it has a strong homology with a chain of hemoglobin. The sequence of the fourth "spot" has little or no homology with any known proteins.

Since N-terminal amino acid sequence analysis of the intact MI protein (third "spot") indicated that the N-terminus of the protein was blocked, it was decided to fragment the protein using a protease and then sequence the resulting peptides. MI protein from four Immobilon PSQ blots was cut out, reduced, alkylated with iodoacetamide, and digested with endoproteinase Lys C (Stone, K. L., M. B. LoPresti, J. M. Crawfrod, R. DeAngelis and K. R. Williams, (1989), *A Practical Guide to Protein and Peptide Purification for Microsequencing*, (P. T. Matsudaira, Ed.), Academic Press, San Diego, Calif., pp. 31047).

Sequencing of the second peak of MI protein obtained after proteolysis of MI protein was more successful, and the following amino acid sequence was obtained:

SEQ ID NO: 1:
Thr Gln Thr Val Xaa Asn Phe Thr Thr Asp Gly Ala Leu Val Gln His
1           5                    10                  15

Gln Glu Xaa Xaa Gly Lys
              20

The sites indicated by an "Xaa" are those in which either an identification could not be confirmed or could not be made at all. Tentative assignments of Cys to site number 5, and Asp to site 19 were made, however. Interestingly, 9 of the 12 C-terminal amino acids in this protein segment correspond to a region of mouse fatty acid binding protein (mFABP), however no significant homology was found for the N-terminal half of the segment.

Sequencing of the third peak obtained from MI protein was as follows:

SEQ ID NO: 2:
Leu Val Val Glu Cys Val Met Asn Asn Val Thr Cys Thr Arg Xaa
1           5                    10                  15

Tyr Glu Lys

Additionally, a tentative assignment of Ile to site number 15 was made. In this case, 13 of the 18 amino acids in this segment correspond to a region of mFABP, with only conservative changes at the 12th, 15th, and 18th amino acids.

Based on this sequencing, it is apparent that MI protein is highly related to mFABP, however it is definitely not identical to it. Mouse fatty acid binding protein is a member of a family that includes fatty acid binding proteins, retinoic acid binding proteins, adipocyte differentiation proteins, and myelin P2 proteins, and, based upon the two sequences identified, it is expected that MI protein is also a member of this family. Thus, since most of the proteins in this family comprise about 131 amino acids, it is further expected that MI protein comprises about 131 amino acids. The fact that MI protein has a close homology to a known protein such as mFABP also is a strong indication that, as the applicants' studies have shown, it is a biologically relevant molecule.

EXAMPLE 10

In order to determine the entire sequence of the MI protein, appropriate oligonucleotide probes for the MI protein were prepared. These oligos were as follows:

5'- CAG CCC GCC CGC ACC -3'

5'- AAA AAA GAA AGA AAC AGT ATG -3'

These oligos were utilized in performing a polymerase chain reaction (PCR) on RNA obtained from human skin which had previously been grafted onto nude mice in the manner previously described. The PCR reaction resulted in the formation of a considerable amount of single-size DNA which codes for MI protein. The isolated DNA was then cloned into a sequencing vector and its sequence determined by known methods. The nucleic acid sequence was as follows, and the corresponding amino acid sequence of MI protein is also shown below the corresponding codons (numerals indicate the position of the amino acids in MI protein):

SEQ ID NO: 3:
```
ATG GCC ACA GTT CAG CAG CTG GAA GGA AGA TGG CGC CTG GTG
Met Ala Thr Val Gln Gln Leu Glu Gly Arg Trp Arg Leu Val
1               5                   10

GAC AGC AAA GGC TTT GAT GAA TAC ATG AAG GAG CTA GGA GTG
Asp Ser Lys Gly Phe Asp Glu Tyr Met Lys Glu Leu Gly Val
15                  20                  25

GGA ATA GCT TTG CGA AAA ATG GGC GCA ATG GCC AAG CCA GAT
Gly Ile Ala Leu Arg Lys Met Gly Ala Met Ala Lys Pro Asp
        30                  35                  40

TGT ATC ATC ACT TGT GAT GGT AAA AAC CTC ACC ATA AAA ACT
Cys Ile Ile Thr Cys Asp Gly Lys Asn Leu Thr Ile Lys Thr
            45                  50                  55

GAG AGC ACT TTG AAA ACA ACA CAG TTT TCT TGT ACC CTG GGA
Glu Ser Thr Leu Lys Thr Thr Gln Phe Ser Cys Thr Leu GLY
                60                  65                  70

GAG AAG TTT GAA GAA ACC ACA GCT GAT GGC AGA AAA ACT CAG
Glu Lys Phe Glu Glu Thr Thr Ala Asp Gly Arg Lys Thr Gln
                    75                  80

ACT GTC TGC AAC TTT ACA GAT GGT GCA TTG GTT CAG CAT CAG
Thr Val Cys Asn Phe Thr Asp Gly Ala Leu Val Gln His Gln
85                  90                  95

GAG TGG GAT GGG AAG GAA AGC ACA ATA ACA AGA AAA TTG AAA
Glu Trp Asp Gly Lys Glu Ser Thr Ile Thr Arg Lys Leu Lys
        100                 105                 110

GAT GGG AAA TTA GTG GTG GAG TGT GTC ATG AAC AAT GTC ACC
Asp Gly Lys Leu Val Val Glu Cys Val Met Asn Asn Val Thr
            115                 120                 125

TGT ACT CGG ATC TAT GAA AAA GTA GAA TAA
Cys Thr Arg Ile Tyr Glu Lys Val Glu
                130             135
```

For the sake of clarity, the sequence for the entire MI protein is shown below:

SEQ ID NO.: 4:
```
Met Ala Thr Val Gln Gln Leu Glu Gly Arg Trp Arg Leu Val
1               5                   10

Asp Ser Lys Gly Phe Asp Glu Tyr Met Lys Glu Leu Gly Val
15                  20                  25

Gly Ile Ala Leu Arg Lys Met Gly Ala Met Ala Lys Pro Asp
        30                  35                  40

Cys Ile Ile Thr Cys Asp Gly Lys Asn Leu Thr Ile Lys Thr
            45                  50                  55

Glu Ser Thr Leu Lys Thr Thr Gln Phe Ser Cys Thr Leu GLY
                60                  65                  70

Glu Lys Phe Glu Glu Thr Thr Ala Asp Gly Arg Lys Thr Gln
                    75                  80

Thr Val Cys Asn Phe Thr Asp Gly Ala Leu Val Gln His Gln
85                  90                  95

Glu Trp Asp Gly Lys Glu Ser Thr Ile Thr Arg Lys Leu Lys
        100                 105                 110

Asp Gly Lys Leu Val Val Glu Cys Val Met Asn Asn Val Thr
            115                 120                 125

Cys Thr Arg Ile Tyr Glu Lys Val Glu
                130             135
```

In order to verify that SEQ ID NO: 4 was indeed MI protein, a protein was recombinantly expressed from SEQ ID NO: 4 using well-known methods. The effect of the recombinantly expressed protein on melanocyte proliferation was then determined by examining the rate of $^3$H-thymidine incorporation in a fashion similar to that of Example 6. A significant dose-dependent inhibition of melanocyte proliferation was observed, clearly indicating that the protein recombinantly expressed from nucleic acid sequence SEQ ID NO: 3 is indeed MI protein. Therefore, the structure of MI protein is shown by SEQ ID NO: 4. As those skilled in the an will recognize, SEQ ID NO:3 can also be employed in well-known methods to verify that any product prepared according to Applicants' synthesis method is indeed MI protein.

EXAMPLE 11

In order to examine the in vivo effects of MI protein on hyperpigmented skin grafts, the entire 13-14 kDa protein mixture containing MI was injected into human skin that had previously been grafted onto nude mice in the manner described previously. Seven mice were utilized in these tests, and these mice had supported the human skin graft for a period of 10 to 12 months prior to the testing. Various degrees of hyperpigmentation were present in the xenografts treated.

The mice to be subjected to the testing were subdivided into an experimental group consisting of five mice, aid a control group consisting of the remaining two mice. The mice in the control group were not given any injections. In the experimental group, injections were made subcutaneously into the left side of the human skin graft at weekly intervals over a five week period. The dosage in each injection consisted of a 50 μl solution containing 2 μg of the protein mixture with the remainder of the solution consisting of normal saline. As an internal control, 50 of normal saline was injected into the right side of the graft at the same intervals. One week after the first set of five injections, the entire testing protocol was repeated. For the second set of five injections, however, the site of injection was changed. During this period, the protein mixture was injected into the dorsal area of the graft and the normal saline (control) was injected into the ventral area of the graft.

Biopsies were taken from the skin grafts before the series of injections, one week after the first set of five injections (but prior to the second set of injections), and after the final injection. These biopsies were taken near the point of injection of both the protein fraction and the normal saline. Biopsies were also taken from the control group.

The number of DOPA positive melanocytes in each biopsy were counted, and the overall results for the testing are shown in Table 1 below. The number of DOPA positive melanocytes is a direct measure of tyrosinase activity within the melanocytes themselves, and the results shown in Table 1 indicate that the protein mixture containing MI protein reduces tyrosinase activity. The reduction in number of DOPA positive melanocytes ranged from 9.0% up to 32.3%. No significant reduction occurred in the biopsies taken from either the control group or from the locations where normal saline was injected into the experimental group.

Visual examination of the mice indicated a marked reduction in hyperpigmentation, particularly at the site of injection, after just two injections of the protein mixture. No such reduction was seen in either the control group, or at the sites of normal saline injection in the experimental group.

TABLE 1

| Mouse | % Reduction in Number of DOPA Positive Melanocytes | |
|---|---|---|
| | Protein Mixture Injection Sites | Saline Injection Sites |
| A | 32.3 | 2.5 |
| B | 29.0 | 1.3 |
| C | 24.6 | 0 |
| D | 9.0 | 0 |
| E | 10.1 | 2.0 |
| F - Control | 0 | 0 |
| G - Control | 0 | 0 |

Sections of several biopsies were also stained with hematoxylin and eosin (H&E) and viewed microscopically in order to examine any morphological changes resulting from the injections of the protein mixture. The experimental and control groups were indistinguishable from one another, and neither group exhibited any evidence of injury or toxicity to either the epidermis or dermis. Thus, MI protein is capable of reducing hyperpigmentation without causing undesired side effects.

EXAMPLE 12

In order to examine the effects of MI protein in preventing or delaying the hyperpigmentation which normally occurs in skin grafts immediately after grafting, the protein mixture utilized in Example 11 was also injected into nude mice which had only supported a human skin graft for 2 weeks. The protocol of Example 11 was followed, except that only the first set of five injections were performed. The protein mixture was injected into the dorsal area of the skin graft, and normal saline was injected into the ventral area. Initial counts of DOPA positive melanocytes were performed just prior to the first injections.

Visual examination of the mice revealed some reduction in pigmentation at the site of protein mixture injection. More importantly, as shown in Table 2, the number of DOPA positive melanocytes was once again significantly reduced in the biopsies taken from the areas at the site of protein mixture injection. In contrast, as expected, the number of DOPA positive melanocytes increased in the biopsies taken from the control group and from the areas at the site of saline injection in the experimental group. This increase ranged from 190% to 300%, while the reduction caused by the protein mixture containing MI ranged from 8.3% to 31.6%. There was also no evidence of toxicity in the mice injected with the protein mixture. This data confirms that MI protein can both prevent or reverse hyperpigmentation, most likely by altering tyrosinase activity, without affecting cell viability.

TABLE 2

| Mouse | % Change in Number of DOPA Positive Melanocytes | |
|---|---|---|
| | Protein Mixture Injection Sites | Saline Injection Sites |
| H | −31.6 | +230 |
| I | −17.5 | +300 |
| J | −11.2 | +210 |
| K | −27.5 | +190 |
| L | −8.3 | +200 |
| M - Control | >200 | +240 |
| N - Control | >200 | +228 |

EXAMPLE 13

The in vivo effects of MI protein on normal pigmented mice (C57BL/6) was also examined. This particular type of mouse has proven useful for studying pigmentation and hair growth, since the truncal skin pigmentation in this mouse originates in the melanocytes of the hair follicles and not the epidermis. Once these hair follicles are plucked, the underlying skin becomes less pigmented due to the reduction in melanocytes. Although the hair follicles resume growth immediately after plucking, repigmentation of the skin does not occur until five or six days later. Thus, this mouse is a good model for examining the effect of MI protein in delaying repigmentation.

Five C57BL/6 mice were employed, and the hair follicles were plucked from small areas on the right and left dorsal side of each. The protein mixture utilized in Example 11 (50 µl containing 2 µg protein mixture) was injected subcutaneously into the left dorsal area of each mouse where the hair follicles had been removed. As a control, an electroeluted 13 to 14 kDa protein fraction obtained from normal human skin (prior to any grafting) was injected into the right dorsal area of each mouse. This protein fraction from normal human skin was obtained in the same manner as that described previously. The injections were given once a day for five days. Photographs were taken each day to monitor skin color changes, and biopsies were taken from both the right and left dorsal portions of each animal.

The left dorsal area into which the protein mixture containing MI protein had been injected showed a reduction in skin color after only 2 injections. No significant reduction in skin color was observed in the right dorsal area. Additionally, the appearance of new hair follicles was also delayed in the left dorsal areas as compared to the right (control).

H&E staining patterns appeared normal for the biopsies from both the right and left dorsal areas, and no morphological differences between the two were observed. There was also no evidence of toxicity, however the biopsies from the left dorsal area into which the protein mixture containing MI protein had been injected showed a reduced staining of melanin in the hair follicles (as shown by DOPA staining).

B. Pharmaceutical and Cosmetic Compositions and Methods

As used herein, "topical application" means directly laying on or spreading on outer skin, "cutaneous injection" means introduction of a substance beneath or within the skin by a hypodermic needle, and "comprising" means that other steps and other ingredients which do not affect the end result can be added. This latter term thus encompasses the terms "consisting of" and "consisting essentially of".

The present invention further relates to a composition comprising a) a substantially pure protein for inhibiting melanogenesis in pigmentary cells, or an active melanogenesis inhibiting segment, derivative or analog thereof, said protein having a molecular weight of about 14,000, an isoelectric point of between about 7.2 and about 7.5, and amino acid sequence SEQ ID NO.: 4; and b) a cosmetically- or pharmaceutically-acceptable carrier. In one embodiment of the invention, the carrier is an injectable carrier. In another embodiment of the invention, the carrier is a topical carrier.

The compositions of the present invention comprise a solid, semi-solid or liquid cosmetically and/or physiologically acceptable carrier to enable the MI protein, or active segment, derivative, or analog thereof, to be delivered to the desired target at an appropriate concentration. The carrier can itself be inert or it can possess physiological or pharmaceutical benefits of its own. The nature of the carrier will be dictated by the method chosen for administration of the composition. A safe and effective mount of carrier is preferably from about 50% to about 99.9999%, more preferably from about 90% to about 99.9% of the composition. Variations in formulation of these carriers will result in a wide variety of products which fall within the scope of the present invention. The method of administration of the MI protein, or active segment thereof, composition may range from internal methods such as injection to external topical methods.

A preferred method of administration of the MI protein, or active segment thereof, is by cutaneous injection. The carrier for facilitation of such administration would preferably comprise water or a saline solution, preferably an isotonic saline solution.

A more preferred method of administration of the MI protein or active segment thereof is by topical application. The topical pharmaceutical compositions of the present invention may be made into a wide variety of product types. These include, but are not limited to lotions, creams, beach oils, gels, sticks, sprays, ointments, pastes, mousses and cosmetics. These product types may comprise several types of carrier systems including, but not limited to solutions, emulsions, gels and solids.

Topical pharmaceutical compositions of the present invention further comprise from about 2% to about 50% of a topical pharmaceutically-acceptable emollient. As used herein, "emollients" refer to materials used for the prevention or relief of dryness, as well as for .the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials. Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol.

The present invention further relates to a method for inhibiting melanogenesis in mammalian skin and/or hair. Such a method comprises treating the skin and/or hair with a safe and effective amount of the MI protein, or active segment, derivative or analog thereof. The amount of MI protein, or active segment thereof, and frequency of treatment will vary widely depending upon the level of pigmentation and/or melanogenesis already in existence in the subject and the amount of melanogenesis inhibition desired.

A preferred method of treating the skin and/or hair is via cutaneous injection of a safe and effective amount of the MI protein, or active segment thereof, to inhibit melanogenesis in mammalian skin and/or hair. The carrier for injectable administration of the MI protein, or active segment thereof, would preferably comprise water or a saline solution. The amount of MI protein, or active segment thereof, and the frequency of cutaneous injection can vary widely, depending on personal needs. As an example of treatment by cutaneous injection, it is suggested that a composition suitable for cutaneous injection comprising the MI protein, or active segment thereof, be cutaneously injected from once per day to once every six months, preferably from three times per week to once per month, more preferably from once per week to twice per month. The composition for cutaneous injection will contain from about 0.0001% to about 10%, preferably from about 0.001% to about 5%, more preferably from about 0.01% to about 1% of the MI protein. The period of injections would be over a period of from about one month to about ten years, preferably from about three months to about two years, more preferably from about six months to about one year, thereby resulting in inhibition of melanogenesis in mammalian skin and/or hair.

A more preferred method of treating the skin and/or hair is via topical application of a safe and effective amount of the MI protein, or active segment thereof, to inhibit melanogenesis in mammalian skin and/or hair. The amount of MI protein, or active segment thereof, and frequency of topical application to the skin and/or hair can vary widely, depending upon personal needs, but it is suggested as an example that topical application range from about once per week to about 10 times daily, preferably from about twice per week to about 4 times daily, more preferably from about 3 times a week to about twice daily, most preferably about once per day. The composition for topical application will comprise from about 0.001% to about 20%, preferably from about 0.01% to about 10%, more preferably from about 0.1% to about 5% of the MI protein, or active segment, derivative or analog thereof. The period of topical application would preferably be over a period of from about one month to about ten years, more preferably from about three months to about two years, more preferably still from about six months to about one year, thereby resulting in inhibition of melanogenesis in mammalian skin and/or hair.

The following examples further describe and demonstrate certain preferred embodiments within the scope of the present invention. The examples are given solely for the purpose of illustration, and are not to be construed as limitations of the present invention since many variations thereof are possible without departing from its spirit and scope. These prospective example merely demonstrate how the melanogenic inhibitor of the present invention may be employed.

EXAMPLE 14

An oil-in-water emulsion is prepared by combining the following components utilizing conventional mixing techniques.

| Component | Percent by Weight of Composition |
| --- | --- |
| Deionized water | Quantum sufficit |
| Glycerin | 3 |
| Methyl paraben | 0.2 |
| MI protein | 0.1 |
| Steareth 20 (Brij 78R) | 1 |
| Glyceryl monostearate and PEG 100 (Arlacel 165R) | 0.5 |
| Carbopol 940 (B. F. Goodrich, Cleveland, OH) | 0.2 |
| 99% triethanolamine | 0.2 |
| Cetyl alcohol | 1.0 |
| Stearyl alcohol | 1.0 |
| Propyl paraben | 0.1 |
| Diisopropyldimerate | 2.0 |
| C12–C15 alcohol benzoate | 6.0 |
| Imidazolidinol urea | 0.3 |

This composition is useful for topical application to inhibit melanogenesis in skin and/or hair. An amount of the composition sufficient to deposit about 0.01 mg/cm$^2$ of the MI protein to the skin and/or hair follicles is used. The composition is applied once per day for the subject's lifetime.

EXAMPLE 15

A clear gel is prepared by combining the following components utilizing conventional mixing techniques.

| Component | Percent by Weight of Composition |
| --- | --- |
| Deionized water | Quantum sufficit |
| Carbopol 980 (B. F. Goodrich, Cleveland, OH) | 0.5 |
| Disodium EDTA | 0.02 |
| SEQ ID NO: 1 | 0.5 |
| 99% triethanolamine | 0.5 |
| Propylene glycol | 3.0 |
| Methyl paraben | 0.2 |

This composition is useful for topical application to inhibit melanogenesis in skin and/or hair. An amount of the composition sufficient to deposit about 0.01 mg/cm$^2$ of MI protein active segment to the skin and/or hair follicles is used. The composition is applied three times per day over a six-month period.

EXAMPLE 16

An oil-in-water polymer emulsion is prepared by combining the following components utilizing conventional mixing techniques.

| Component | Percent by Weight of Composition |
| --- | --- |
| Deionized water | Quantum sufficit |
| Carbopol 954 (B. F. Goodrich, Cleveland, OH) | 0.2 |
| Pemulen TR-2 (B. F. Goodrich, Cleveland, OH) | 0.15 |
| Glycerin | 3.0 |
| SEQ ID NO: 2 | 0.75 |
| 99% triethanolamine | 0.35 |
| Cetyl palmitate | 2.0 |
| Stearoxy trimethyl silane and stearyl alcohol | 1.0 |
| Squalane | 6.0 |
| Propyl paraben | 0.1 |
| Methyl paraben | 0.2 |
| Imidazolidinol urea | 0.3 |

This composition is useful for topical application to inhibit melanogenesis. An amount of the composition sufficient to deposit 0. 1 mg/cm$^2$MI protein active segment to the skin and/or hair follicles is used. The composition is applied once per week over a one-year period.

EXAMPLE 17

An oil-in-water microemulsion is prepared by combining the following components utilizing conventional mixing techniques.

| Component | Percent by Weight of Composition |
| --- | --- |
| Deionized water | Quantum sufficit |
| MI protein | 1.0 |
| PEG4 sorbitan monolaurate | 22.5 |
| PEG5 sorbitan monolaurate | 2.5 |
| Cetearyl octanoate | 25.0 |
| DMDM hydantoin and 3-iodo-2-propynyl butyl carbamate (glydant plus) | 0.2 |

This composition is useful for topical application to inhibit melanogenesis. An amount of the composition sufficient to deposit 0.4 mg/cm$^2$MI protein to the skin and/or hair follicles is used. The composition is applied three times per week over a five-year period.

It will be understood that modifications may be made without departing from the spirit of the present invention.

Thus, the applicants' invention is understood to encompass not only the entire MI protein, as well as methods of using and producing the same, but also active segments of MI protein. Also, derivatives and analogs of MI protein can be prepared by those skilled in the art, such as by making conservative changes in one or more of the amino acids in the MI sequence. Additionally, non-peptide mimetics could be modeled after active segments of MI protein, and thus these mimetics do not depart from the spirit of the present invention. Accordingly, the scope of the present invention should be considered in terms of the following claims, and it is understood not to be limited to that shown and described in the specification.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 21
        ( B ) TYPE: Amino Acid
        ( D ) TOPOLOGY: Linear ( i i ) MOLECULE TYPE: Protein ( x i ) SEQUENCE DESCRIPTION: SEQ ID NO:1:

| Thr | Gln | Thr | Val | Xaa | Asn | Phe | Thr | Asp | Gly | Ala | Leu | Val | Gln | Hi |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Gln | Glu | Xaa | Xaa | Gly | Lys |     |     |     |     |     |     |     |     |     |
| 20  |     |     |     |     |     |     |     |     |     |     |     |     |     |     |

( 2 ) INFORMATION FOR SEQ ID NO: 2:

( i ) SEQUENCE CHARACTERISTICS:
        ( A ) LENGTH: 18
        ( B ) TYPE: Amino Acid
        ( D ) TOPOLOGY: Linear ( i i ) MOLECULE TYPE: Protein ( x i ) SEQUENCE DESCRIPTION: SEQ ID NO:2:

| Leu | Val | Val | Glu | Cys | Val | Met | Asn | Asn | Val | Thr | Cys | Thr | Arg | Xa |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Tyr | Glu | Lys |     |     |     |     |     |     |     |     |     |     |     |     |

( 2 ) INFORMATION FOR SEQ ID NO: 3:

( i ) SEQUENCE CHARACTERISTICS:
        ( A ) LENGTH: 408 bases
        ( B ) TYPE: nucleic acid
        ( C ) STRANDEDNESS: Single
        ( D ) TOPOLOGY: Unknown ( x i ) SEQUENCE DESCRIPTION: SEQ ID NO:3:

| ATG | GCC | ACA | GTT | CAG | CAG | CTG | GAA | GGA | AGA | TGG | CGC | CTG | GTG | 42 |
|-----|-----|-----|-----|-----|-----|-----|-----|-----|-----|-----|-----|-----|-----|-----|
| Met | Ala | Thr | Val | Gln | Gln | Leu | Glu | Gly | Arg | Trp | Arg | Leu | Val |    |
| 1   |     |     |     | 5   |     |     |     |     | 10  |     |     |     |     |    |
| GAC | AGC | AAA | GGC | TTT | GAT | GAA | TAC | ATG | AAG | GAG | CTA | GGA | GTG | 84 |
| Asp | Ser | Lys | Gly | Phe | Asp | Glu | Tyr | Met | Lys | Glu | Leu | Gly | Val |    |
| 15  |     |     |     |     | 20  |     |     |     |     | 25  |     |     |     |    |
| GGA | ATA | GCT | TTG | CGA | AAA | ATG | GGC | GCA | ATG | GCC | AAG | CCA | GAT | 12 |
| Gly | Ile | Ala | Leu | Arg | Lys | Met | Gly | Ala | Met | Ala | Lys | Pro | Asp |    |
|     | 30  |     |     |     |     | 35  |     |     |     |     | 40  |     |     |    |
| TGT | ATC | ATC | ACT | TGT | GAT | GGT | AAA | AAC | CTC | ACC | ATA | AAA | ACT | 16 |
| Cys | Ile | Ile | Thr | Cys | Asp | Gly | Lys | Asn | Leu | Thr | Ile | Lys | Thr |    |
|     |     | 45  |     |     |     |     | 50  |     |     |     |     | 55  |     |    |
| GAG | AGC | ACT | TTG | AAA | ACA | ACA | CAG | TTT | TCT | TGT | ACC | CTG | GGA | 21 |

| | | | | | | | | | | | | |
|---|---|---|---|---|---|---|---|---|---|---|---|---|
| Glu | Ser | Thr | Leu<br>60 | Lys | Thr | Thr | Gln | Phe<br>65 | Ser | Cys | Thr | Leu | GLY<br>70 |
| GAG<br>Glu | AAG<br>Lys | TTT<br>Phe | GAA<br>Glu | GAA<br>Glu<br>75 | ACC<br>Thr | ACA<br>Thr | GCT<br>Ala | GAT<br>Asp | GGC<br>Gly<br>80 | AGA<br>Arg | AAA<br>Lys | ACT<br>Thr | CAG<br>Gln | 25 |
| ACT<br>Thr<br>85 | GTC<br>Val | TGC<br>Cys | AAC<br>Asn | TTT<br>Phe | ACA<br>Thr<br>90 | GAT<br>Asp | GGT<br>Gly | GCA<br>Ala | TTG<br>Leu | GTT<br>Val<br>95 | CAG<br>Gln | CAT<br>His | CAG<br>Gln | 29 |
| GAG<br>Glu | TGG<br>Trp<br>100 | GAT<br>Asp | GGG<br>Gly | AAG<br>Lys | GAA<br>Glu | AGC<br>Ser<br>105 | ACA<br>Thr | ATA<br>Ile | ACA<br>Thr | AGA<br>Arg<br>110 | AAA<br>Lys | TTG<br>Leu | AAA<br>Lys | 33 |
| GAT<br>Asp | GGG<br>Gly | AAA<br>Lys<br>115 | TTA<br>Leu | GTG<br>Val | GTG<br>Val | GAG<br>Glu | TGT<br>Cys<br>120 | GTC<br>Val | ATG<br>Met | AAC<br>Asn | AAT<br>Asn | GTC<br>Val<br>125 | ACC<br>Thr | 37 |
| TGT<br>Cys | ACT<br>Thr | CGG<br>Arg | ATC<br>Ile<br>130 | TAT<br>Tyr | GAA<br>Glu | AAA<br>Lys | GTA<br>Val | GAA<br>Glu<br>135 | TAA | | | | | 40 |

( 2 ) INFORMATION FOR SEQ ID NO: 4:

( i ) SEQUENCE CHARACTERISTICS:
        ( A ) LENGTH: 135
        ( B ) TYPE: Amino Acid
        ( D ) TOPOLOGY: Linear ( i i ) MOLECULE TYPE: Protein ( x i ) SEQUENCE DESCRIPTION: SEQ ID NO:4:

| | | | | | | | | | | | | |
|---|---|---|---|---|---|---|---|---|---|---|---|---|
| Met<br>1 | Ala | Thr | Val | Gln<br>5 | Gln | Leu | Glu | Gly | Arg<br>10 | Trp | Arg | Leu | Val |
| Asp<br>15 | Ser | Lys | Gly | Phe | Asp<br>20 | Glu | Tyr | Met | Lys | Glu<br>25 | Leu | Gly | Val |
| Gly | Ile<br>30 | Ala | Leu | Arg | Lys | Met<br>35 | Gly | Ala | Met | Ala | Lys<br>40 | Pro | Asp |
| Cys | Ile | Ile<br>45 | Thr | Cys | Asp | Gly | Lys<br>50 | Asn | Leu | Thr | Ile | Lys<br>55 | Thr |
| Glu | Ser | Thr | Leu<br>60 | Lys | Thr | Thr | Gln | Phe<br>65 | Ser | Cys | Thr | Leu | GLY<br>70 |
| Glu | Lys | Phe | Glu | Glu<br>75 | Thr | Thr | Ala | Asp | Gly<br>80 | Arg | Lys | Thr | Gln |
| Thr<br>85 | Val | Cys | Asn | Phe | Thr<br>90 | Asp | Gly | Ala | Leu | Val<br>95 | Gln | His | Gln |
| Glu | Trp<br>100 | Asp | Gly | Lys | Glu | Ser<br>105 | Thr | Ile | Thr | Arg | Lys<br>110 | Leu | Lys |
| Asp | Gly | Lys<br>115 | Leu | Val | Val | Glu | Cys<br>120 | Val | Met | Asn | Asn | Val<br>125 | Thr |
| Cys | Thr | Arg | Ile<br>130 | Tyr | Glu | Lys | Val | Glu<br>135 | | | | | |

( 2 ) INFORMATION FOR SEQ ID NO: 5:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: Unknown ( x i ) SEQUENCE DESCRIPTION: SEQ ID NO:5:

| | | | | |
|---|---|---|---|---|
| CAG<br>Gln<br>1 | CCC<br>Pro | GCC<br>Ala | CGC<br>Arg | ACC<br>Thr | 15 |

(2) INFORMATION FOR SEQ ID NO: 6:

(i) SEQUENCE CHARACTERISTICS:
        (A) LENGTH: 21 bases
        (B) TYPE: nucleic acid
        (C) STRANDEDNESS: single
        (D) TOPOLOGY: Unknown (xi) SEQUENCE DESCRIPTION: SEQ ID NO:6:

| AAA | AAA | GAA | AGA | AAC | AGT | ATG | 21 |
|-----|-----|-----|-----|-----|-----|-----|----|
| Lys | Lys | Glu | Arg | Asn | Ser | Met |    |
| 1   |     |     |     | 5   |     |     |    |

What is claimed is:

1. A method of producing a protein for inhibiting melanogenesis in pigmentary cells comprising the steps of:

(a) grafting mammalian skin onto a live host;

(b) permitting said mammalian skin to remain on said live host for a predetermined period of time;

(c) removing said mammalian skin from said host; and (d) extracting said protein from said skin wherein said protein has a molecular weight in the range of about 13 to about 14 kDa.

2. The method of claim 1, wherein said host is a nude mouse.

3. The method of claim 2, wherein the mammalian skin is human skin.

4. The method of claim 3, wherein said human skin is permitted to remain on said host for at least two weeks.

5. The method of claim 4, wherein said extracting of said protein comprises the following steps:

(a) extracting a skin protein extract from said skin using physiological saline;

fractionating said skin protein extract by ion exchange chromatography (b) into at least two solutions, wherein at least one of said solutions comprises said protein;

(c) subjecting one of said solutions comprising said protein to two-dimensional SDS-PAGE to isolate said protein into a spot on a polyacrylamide gel; and (d) electroeluting said protein from said spot.

6. The method of claim 5, wherein said protein has the following amino acid sequence: SEQ ID NO: 4.

7. A substantially pure protein for inhibiting melanogenesis in pigmentary cells, said protein having the following amino acid sequence: SEQ ID NO: 4, or an active melanogenesis inhibiting segment, derivative or analog thereof.

8. A substantially pure protein for inhibiting melanogenesis in pigmentary cells, said protein having the following amino acid sequence: SEQ ID NO: 4.

9. A method of controlling melanogenesis in pigmentary cells comprising the steps of:

(a) providing an effective amount of a melanogenic inhibitor comprising a melanogenic inhibitor protein, or an active melanogenesis inhibiting segment, derivative or analog thereof, said protein having the following amino acid sequence: SEQ ID NO: 4;

(b) combining said melanogenic inhibitor with a suitable carrier; and (c) applying said combined melanogenic inhibitor to pigmentary cells to be controlled.

10. The method of claim 9, wherein said applying step is performed by injection.

11. The method of claim 9, wherein said applying step is performed by topical application.

12. The method of claim 11, wherein said pigmentary cells are skin pigmentary cells.

13. The method of claim 11, wherein said pigmentary cells are hair pigmentary cells.

14. The method of claim 10, wherein said melonogenic inhibitor is said melanogenic inhibitor protein.

15. The method of claim 11, wherein said melonogenic inhibitor is said melanogenic inhibitor protein.

16. A method of eradicating melanoma cells comprising the steps of:

(a) providing an effective amount of a melanogenic inhibitor comprising a melanogenic inhibitor protein, or an active melanogenesis inhibiting segment, derivative or analog thereof, said protein having the following amino acid sequence: SEQ ID NO: 4;

(b) combining said melanogenic inhibitor with a suitable carrier; and (c) applying said combined melanogenic inhibitor to melanoma cells to be eradicated.

17. The method of claim 16, wherein said melanogenic inhibitor is said melanogenic inhibitor protein.

18. The method of claim 17, wherein said applying step is performed by injection.

19. The method of claim 17, wherein said applying step is performed by topical application.

\* \* \* \* \*

UNITED STATES PATENT AND TRADEMARK OFFICE
CERTIFICATE OF CORRECTION

PATENT NO. : 5,719,126
DATED : February 17, 1998
INVENTOR(S) : James J. Nordlund & Jamal Z. Farooqui It is certified that error appears in the above-indentified patent and that said Letters Patent is hereby corrected as shown below:

Column 25, line 37 (claim 5), before the word "fractionating" insert --(b)--

Column 25, line 39 (claim 5), before the word "into" delete "(b)"

Signed and Sealed this

Sixteenth Day of June, 1998

Attest:

BRUCE LEHMAN

*Attesting Officer*     *Commissioner of Patents and Trademarks*